United States Patent [19]

Willis et al.

[11] Patent Number: 4,788,650
[45] Date of Patent: Nov. 29, 1988

[54] CONTINUOUS COLOR MEASUREMENT FOR SMALL FABRIC SAMPLES

[75] Inventors: Robert F. Willis; Robert H. Best, both of Greensboro; Vernon T. Daniel, Oak Ridge; Roland L. Connelly; Ann Griesinger, both of Greensboro, all of N.C.

[73] Assignee: Burlington Industries, Inc., Greensboro, N.C.

[21] Appl. No.: 909,331

[22] Filed: Sep. 19, 1986

[51] Int. Cl.⁴ .............................................. G01N 21/25
[52] U.S. Cl. .................................... 364/526; 364/470; 356/429; 250/571; 250/226
[58] Field of Search ............... 364/526, 403, 470, 571; 356/402, 429, 238; 250/226, 571

[56] References Cited

U.S. PATENT DOCUMENTS

| | | | |
|---|---|---|---|
| 3,388,261 | 6/1968 | Roberts et al. | 250/224 |
| 3,531,208 | 9/1970 | Ward | 364/526 |
| 3,935,436 | 1/1976 | Holschlag et al. | 235/151.35 |
| 4,103,177 | 7/1978 | Sandford et al. | 250/562 |
| 4,346,997 | 8/1982 | Willis | 356/244 |
| 4,349,279 | 9/1982 | Jung | 356/402 |
| 4,402,611 | 9/1983 | Yuasa | 364/526 |
| 4,418,390 | 11/1983 | Smith et al. | 364/526 |
| 4,439,038 | 3/1984 | Mactaggart | 364/526 |
| 4,494,875 | 1/1985 | Schramm et al. | 356/402 |
| 4,680,205 | 7/1987 | Lerner et al. | 356/429 |
| 4,688,178 | 8/1987 | Connelly et al. | 364/470 |

OTHER PUBLICATIONS

Hunter Lab brochure entitled "From Hunter Lab . . . New Continuous Textile Shade Monitor TM TSM", 6 pages.
"High Technology" magazine, Sep. 1986, p. 9, Color Sense for Industry.

Primary Examiner—Parshotam S. Lall
Assistant Examiner—V. N. Trans
Attorney, Agent, or Firm—Nixon & Vanderhyde

[57] ABSTRACT

The average color, and excursions outside predetermined acceptable color limits, of non-solid-shade fabrics, such as denim, can be determined utilizing a filter colorimeter, an A/D convertor, and computer. A swatch of fabric having a length greater than its width is continuously moved past the colorimeter, and is continuously sampled at the rate of at least about 100 readings per second until the length of the entire swatch has been sampled and analog signals have been generated for all readings. Analog signals are continuously passed from the colorimeter to the A/D convertor, and from the convertor as digital signals to storage in the computer. After sampling is completed the stored digital signals are analyzed. The voltage of the electric light source of the colorimeter is monitored to calibrate the digital signals depending on the voltage to the light source. The swatch is moved with respect to the colorimeter by an assembly including swatch detectors, swatch moving apparatus including a pair of rollers, connected by a belt and driven by a motor, and a device for adjusting the swatch moving apparatus to accommodate swatches of different dimensions.

20 Claims, 5 Drawing Sheets

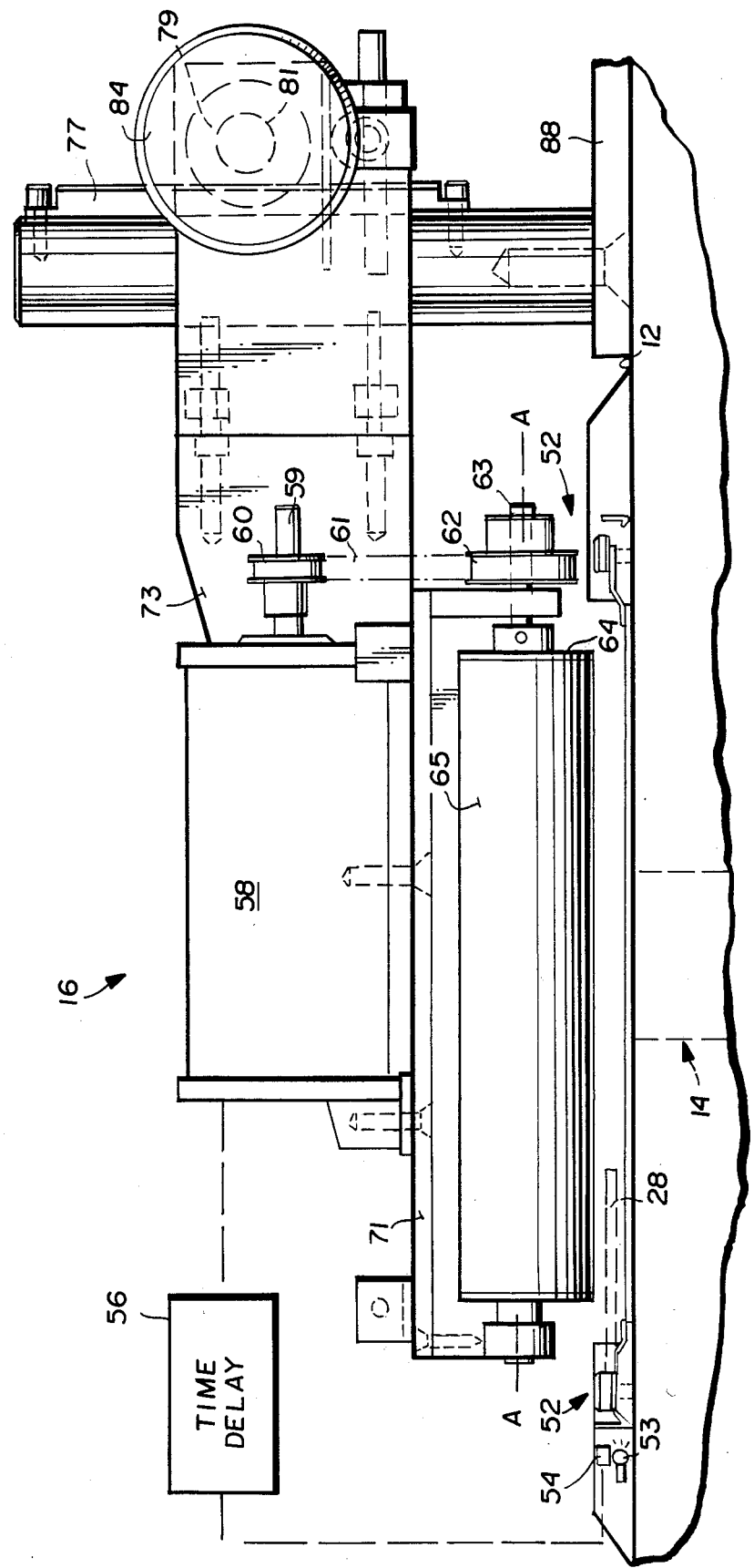

CONTINUOUS COLOR MEASUREMENT FOR SMALL FABRIC SAMPLES

BACKGROUND AND SUMMARY OF THE INVENTION

In the production of colored fabrics, it is highly desirable to test the color of the fabrics to be sure that the dyeing operation is working satisfactorily, and to ensure that the color of the fabric is appropriate for the end use desired.

Perhaps the most common commercial practice for measuring the color of rolls of fabric comprises cutting a six-inch full-width swatch from the end of each roll, and measuring the swatch in one or two spots and averaging the readings to obtain a representative color value for the roll. Most color instrumentation that is used for this purpose is capable of viewing only a relatively small area (e.g. about 1–3 square inches). While this approach is acceptable for solid shade fabrics, for fabrics having inherent color variations within relatively small areas, such as denim, plaids, checks, patterned, and multi-color fabrics (i.e. non-solid-shade fabrics) it is not. In commercial practice non-solid-shade fabrics cannot be reliably measured without extensive reading and averaging of results taken from many different locations on the swatch, a time consuming and commercially impractical approach.

Other commercially available color monitoring equipment is designed to sample a "roll" of fabric without the necessity of cutting swatches by traversing laterally at the same time that the cloth moves longitudinally beneath it, taking a reading each time it encounters the left side, center, and right side of the fabric, taking readings at speeds of up to seven readings per second. Such equipment cannot provide detailed analysis of shade changes across the width of the fabric, and thus the apparatus is limited, for practical use, to solid shade fabrics.

According to the present invention, it is possible for the first time to accurately determine color properties, such as average color and/or excursions outside predetermined acceptable color limits, of non-solid-shade fabrics. Typical non-solid-shade fabrics on which the invention may be utilized include denim, patterned fabrics (e.g. checks and plaids), crushed velours, pile fabrics, and fabrics containing fancy (slub) yarns. This is accomplished according to the invention by continuously sampling a fabric swatch, typically having a six-inch width and a 60-inch length (corresponding to the 60-inch width of a fabric roll). Typically about 400–1,000 readings would be taken along the length of the swatch. These readings can be taken in a fast and effective manner according to the invention by continuously moving the swatch with respect to a colorimeter head, continuously sampling the swatch with the colorimeter head at a rate of at least about 100 readings per second, continuously passing the analog signals from the colorimeter directly to an analog-to-digital (A/D) convertor, continuously converting the analog signals from the colorimeter to digital signals utilizing the A/D convertor and passing the digital signals to storage in a computer (e.g. microprocessor), and after completion of the continuous sampling, analyzing the stored digital signals with the computer to determine average color and/or excursions outside acceptable limits of color. The invention is particularly effective when mechanical apparatus is associated with the colorimeter for continuously moving the fabric swatch with respect to the colorimeter, although movement can be effected by hand.

An advantage of the invention is that the color reading aspects thereof can be readily performed with conventionally available equipment. The colorimeter head itself is a conventional four filter colorimeter head having red, green, and blue filters operatively associated with conventional photo-detectors and in operative association with an electrically powered light source. The colorimeter preferably is of the type manufactured by Hunter Associates Laboratory, Inc., of Reston, Va. However only the head (including the filters, photo-detectors, and light source) of a Hunter colorimeter is utilized, not conventional A/D convertors, microprocessors, or cablings that are associated with it. Rather, according to the invention, an A/D convertor board manufactured by Data Translation Company is utilized, and it is connected up to a DEC microprocessor, such as a Model PDP 11/73. This provides sufficient capacity to continuously receive and store all of the readings from across the entire length of the fabric swatch (e.g. about 400–1,000 readings), and then to perform appropriate analysis after reading is completed.

According to the present invention it is also desirable to monitor the voltage to the light source of the colorimeter head to calibrate the analog signals, and ultimately the digital signals from the A/D convertor, depending upon the voltage to the light source. This can be effected utilizing a simple voltage divider operatively connected to the power lines to the light source, and to a DB 25-5 connector, or the like, which is operatively connected to the colorimeter head, photo-detectors and ultimately to the A/D board.

The invention also contemplates apparatus for moving a swatch of fabric with respect to the colorimeter. Typically the colorimeter head has a housing with a generally planar surface having a viewing port therein and over which the fabric swatch, in non-rigid form (i.e. unbacked) is passed. Swatch detection means, such as a pair of optical detectors, are mounted on the generally planar surface at a first .idse of the viewing port and swatch moving means are mounted on the generally planar surface and extend from the swatch detection means toward and to a second side of the viewing port, opposite the first side, for engaging a swatch of fabric resting on the housing generally planar surface and moving the fabric from the first side of the viewing port to the second side thereof. The swatch moving means includes power means. The swatch moving means preferably comprises first and second rollers that are connected by a belt with one of the rollers driven through a drive mechanism by an electric motor. Adjustment means are provided for adjusting the swatch moving means with respect to the housing surface to accommodate fabric swatches of different dimensions.

In order to allow the sample swatch to be moved across the viewing port in any direction while maintaining an optically acceptable viewing surface it is desirable to provide a positive pressure system such as shown in U.S. Pat. No. 4,346,997 (the disclosure of which is hereby incorporated by reference herein) for the colorimeter head. In such a system, fluid is continuously supplied under pressure to the colorimeter head to exhaust through the viewing port to prevent sample lint and dust from entering the head, to facilitate removal of heat that has been generated by the colorimeter, and to facilitate maintenance of a sample so that a flat, distortion-free surface can be examined; and exhausting the fluid supplied to the head from a location distinct from the viewing port when the viewing port is covered with a sample swatch to be examined.

It is the primary object of the present invention to provide for the effective and accurate determination of average color and/or excursion outside predetermined acceptable color limits for fabrics, including non-solid-shade fabrics. This and other objects of the invention will become clear from an inspection of the detailed description of the invention, and from the appended claims.

BRIEF DESCRIPTION OF THE DRAWINGS

FIG. 5 is a front-end view of the apparatus of FIG. 4.

DETAILED DESCRIPTION OF THE DRAWINGS

Figure 1:
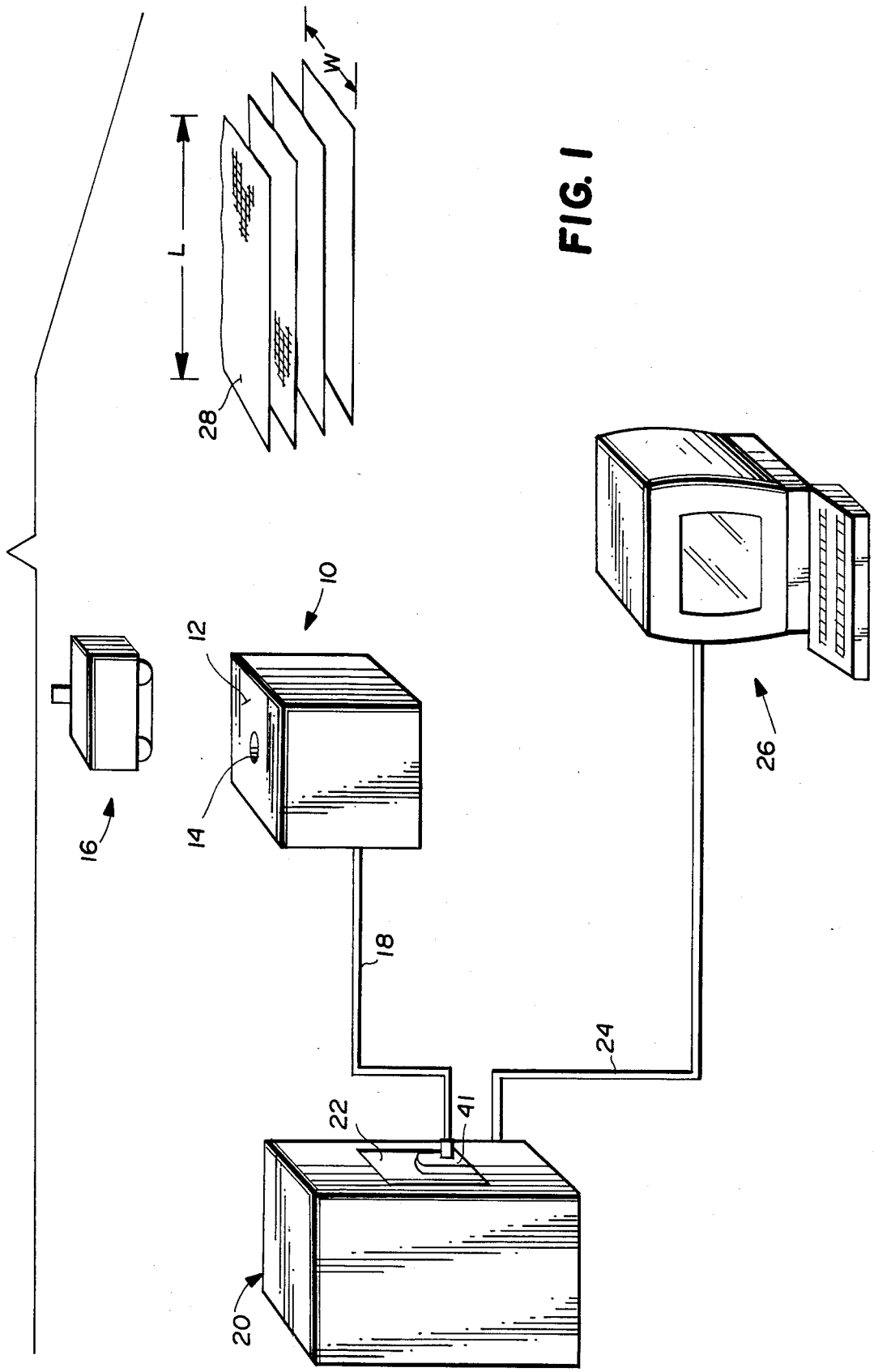
FIG. 1 is a schematic view of the exemplary major components of apparatus according to the present invention and exemplary fabric swatches of which the apparatus is utilized.

The basic components of exemplary apparatus according to the present invention are illustrated schematically in FIG. 1. They include the colorimeter head 10, which is preferably a conventional four-filter colorimeter such as manufactured by Hunter Associates Laboratory, Inc. of Reston, Va. The colorimeter head 10 conventionally includes a generally planar surface 12 with an open viewing port 14 therein. Preferably a mechanical, automatic, swatch feed means 16 is associated with the colorimeter 10. The swatch feed means 16 is, in use, mounted to the surface 12 and conveys a fabric swatch to be analyzed past the viewing port 14. The swatch moving means 16 may be retrofit onto existing colorimeter heads, and will be more fully described hereafter.

The photo-detector output from the colorimeter 10 is connected via analog interface cable 18 to a computer means 20, typically to an A/D convertor 22 which is mounted in the same housing as the computer means 20. The computer means 20 preferably comprises a microprocessor, such as a DEC microprocessor, Model PDP 11/73. The A/D convertor board 22 is preferably one manufactured by Data Translation Company.

The computer means 20 is connected via communications cable 24 to an operator terminal/keyboard 26. An operator can key in information about the fabric swatch to be analyzed, and initiate various controls of the software operating the computer means 20.

The apparatus illustrated in FIG. 1 is utilized for analyzing the color of fabric swatches 28, each having a length L and a width W. The length L is typically significantly greater than the width W, and typically the length L would be greater than 12 inches and continuous samplings would be taken along the entire length L. Commonly, the swatches 28 are cut from the ends of conventional fabric rolls and the dimension L would be about 60 inches, and the dimension W about six inches.

Figure 2:
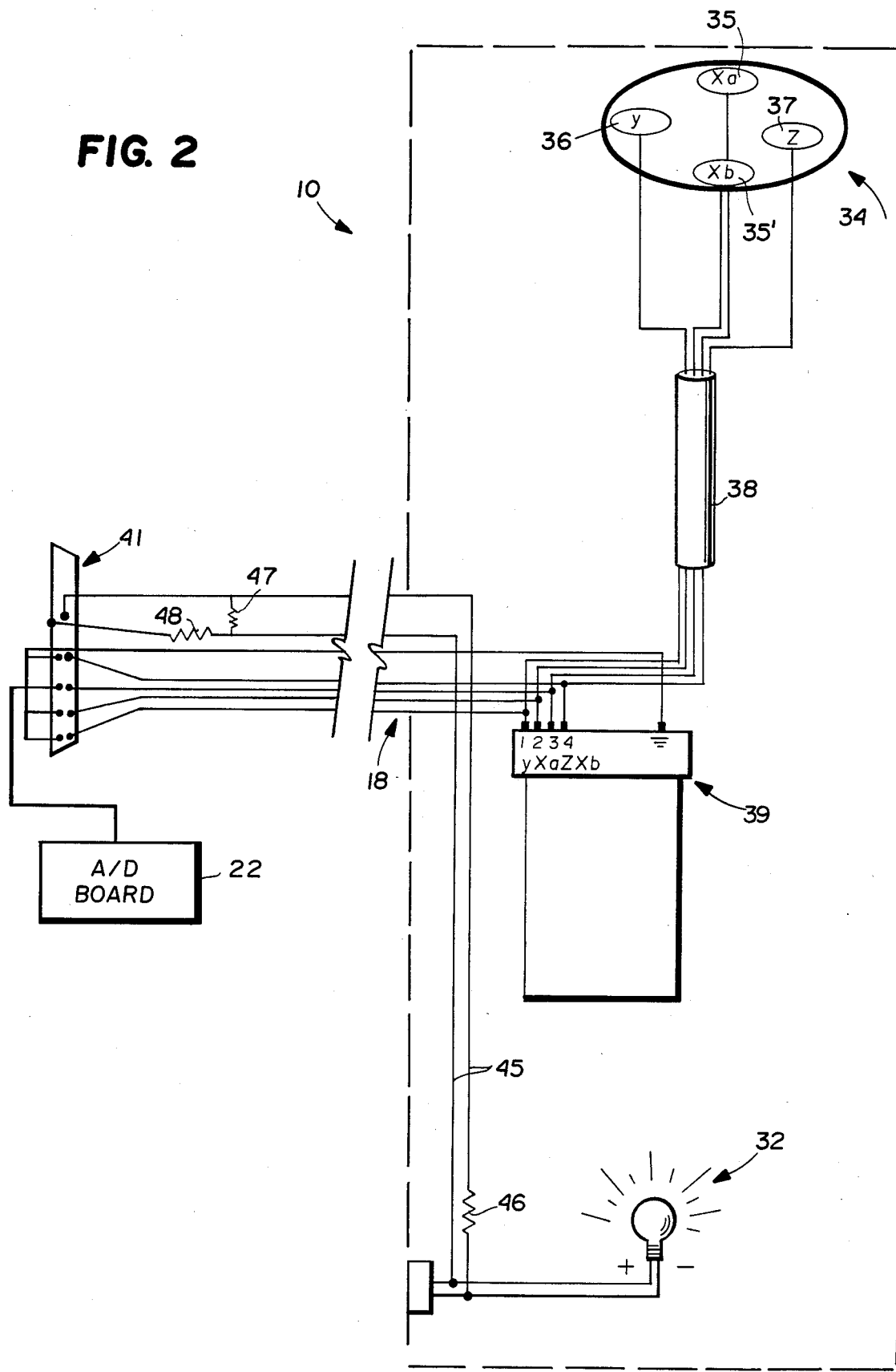
FIG. 2 is a wiring diagram showing the colorimeter and connections to the A/D convertor, according to the invention.

Internal components of the conventional colorimeter head 10 are illustrated in FIG. 2. The filter/detector assembly 34 includes a plurality of filters, preferably a pair of green filters 35, 35', a red filter 36, and a blue filter 37. The filters are operatively associated with photo-detectors 38, and light which is directed onto a swatch 28 to be analyzed is provided from electrically powered light source 32. The photo-detectors 38 are connected to a conventional photo-detector output adjustment board 39, which is operatively connected to the analog interface cable 18. The cable 18 is in turn connected to connector 41, such as a DB25-5 connector, and that in turn is operatively connected to A/D board 22.

According to the present invention, the voltage to the lamp 32 is monitored so as to adjust the analog signals from the colorimeter 10, and thus the digital signals to the computer 20, to enhance the accuracy of the readings. This is accomplished according to the invention by connecting the lines 45 to the lines 43 supplying power to the lamp 32. Associated with the lines 45 are five kilo-ohm resistor 46, two kilo-ohm resistor 47, and three kilo-ohm resistor 48, which provide a simple voltage divider. The lines 45 are operatively connected to the connector 41. In this way ultimately the digital signals to the computer are calibrated to improve their accuracy since they are not dependent upon voltage variations and the powered supplied to the light source 32.

Figure 3:
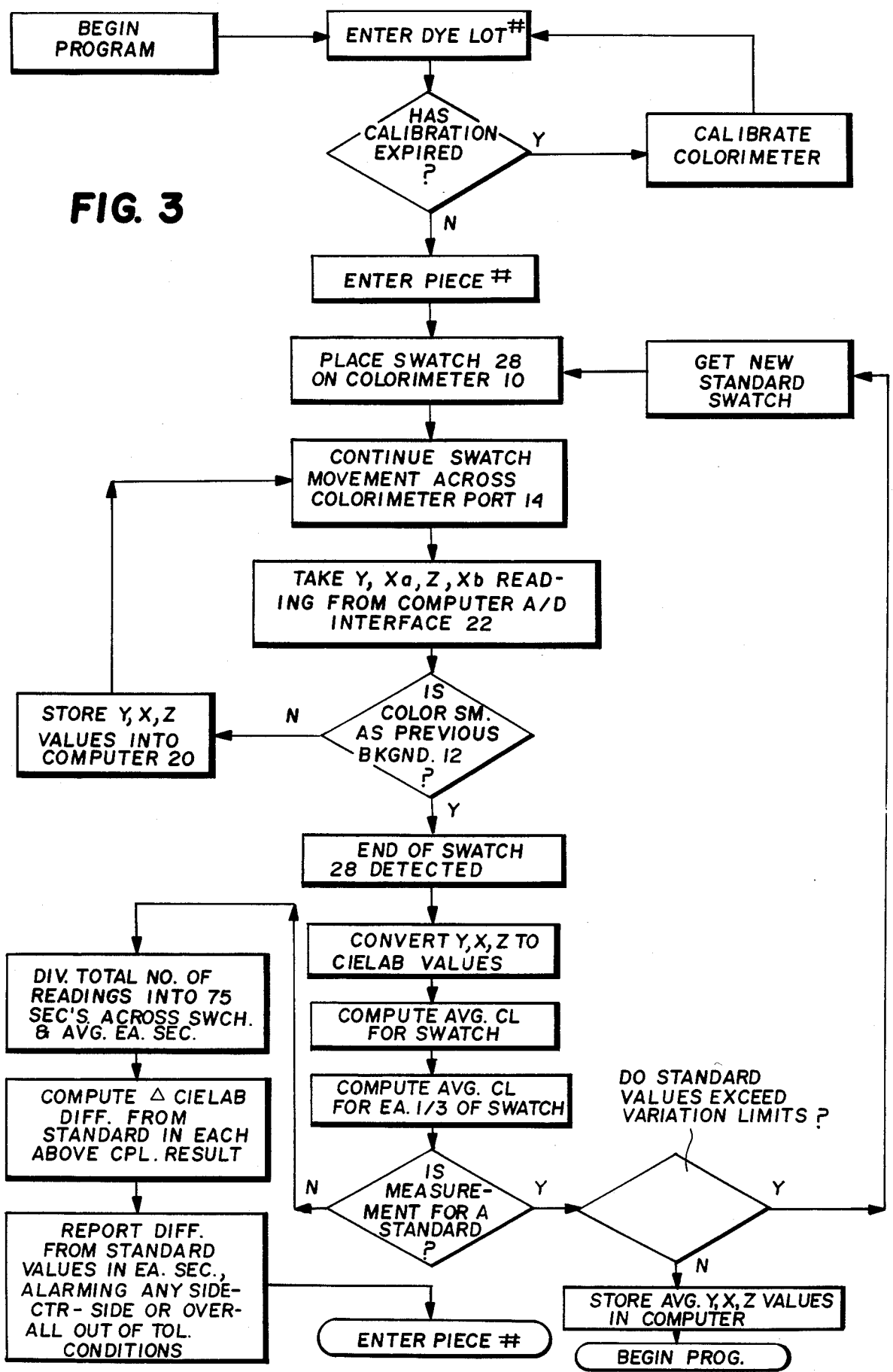
FIG. 3 is a flow diagram illustrating the method carried out by the microprocessor to make the necessary color readings and calculations of average color and/or excursions outside predetermined acceptable color limits, according to the invention.

The flow chart of FIG. 3 schematically illustrates the controlled operation of the computer to function in the manner desired according to the present invention. A swatch 28 is placed on the calibrated colorimeter 10 and is continuously moved across the port 14 with the various filter (34) readings taken from the A/D interface 22. As long as fabric remains over the port 14, the readings are automatically stored in the computer 20. Note that the colorimeter provides a continuous output and the A/D interface can sample all channels at a rate of at least about 100 readings per second, and as the readings are taken and converted to digital signals, they are immediately stored in the computer 20 rather than subjected to analysis at that time.

Once continuous sampling of the length L of the entire swatch 28 has been detected, the Y, X, Z (green, red, and blue) value readings are converted to CIELAB values. That is, the Y, X, and Z values are converted to a color space, providing coordinates in a three dimensional color space for the computer to ultimately act upon. The CIELAB values are then acted upon to provide an average color, and/or excursions outside predetermined acceptable color limits.

Because readings are taken continuously according to the invention, and immediately stored in the computer 20, it is possible to quickly sample the entire length of the swatch 28, rather than a few discreet, spaced portions thereof. For example, since at least about 100 readings are taken per second (e.g. about 500 readings per second), and since about 400–1,000 readings are taken across the length L of the swatch 28, sampling can be done in a matter of a few seconds. This allows accurate measurement of non-solid-shade fabrics, which have inherent color variations over relatively small areas, such as denims, patterned fabrics (e.g. heathers, checks, and plaids), crushed velours, pile fabrics, and fabrics containing fancy (slub) yarns. The ultimate output determined according to the invention can then be used for a variety of purposes such as adjusting dyeing conditions, or with a shade sorting system such as disclosed in co-pending application Ser. No. 773,216 filed Sept. 6, 1985.

To roughly illustrate the advantages obtainable according to the present invention in evaluating side-center-side color differences even of "blotchy" fabrics, such as denim, a 60-inch by 6-inch denim swatch was tested. Ten readings were made on the swatch by conventional means (two readings averaged on a randomly selected area). Standard deviations of $dL^*=0.744$, $dc^*=0.161$, $dh^*=0.077$, were obtained. Ten readings were then made on the same swatch using the continuous read method according to the invention (three second scan), with standard deviations of $dL^*=0.027$, $dc^*=0.013$, and $dh^*=0.007$ obtained.

Figure 4:
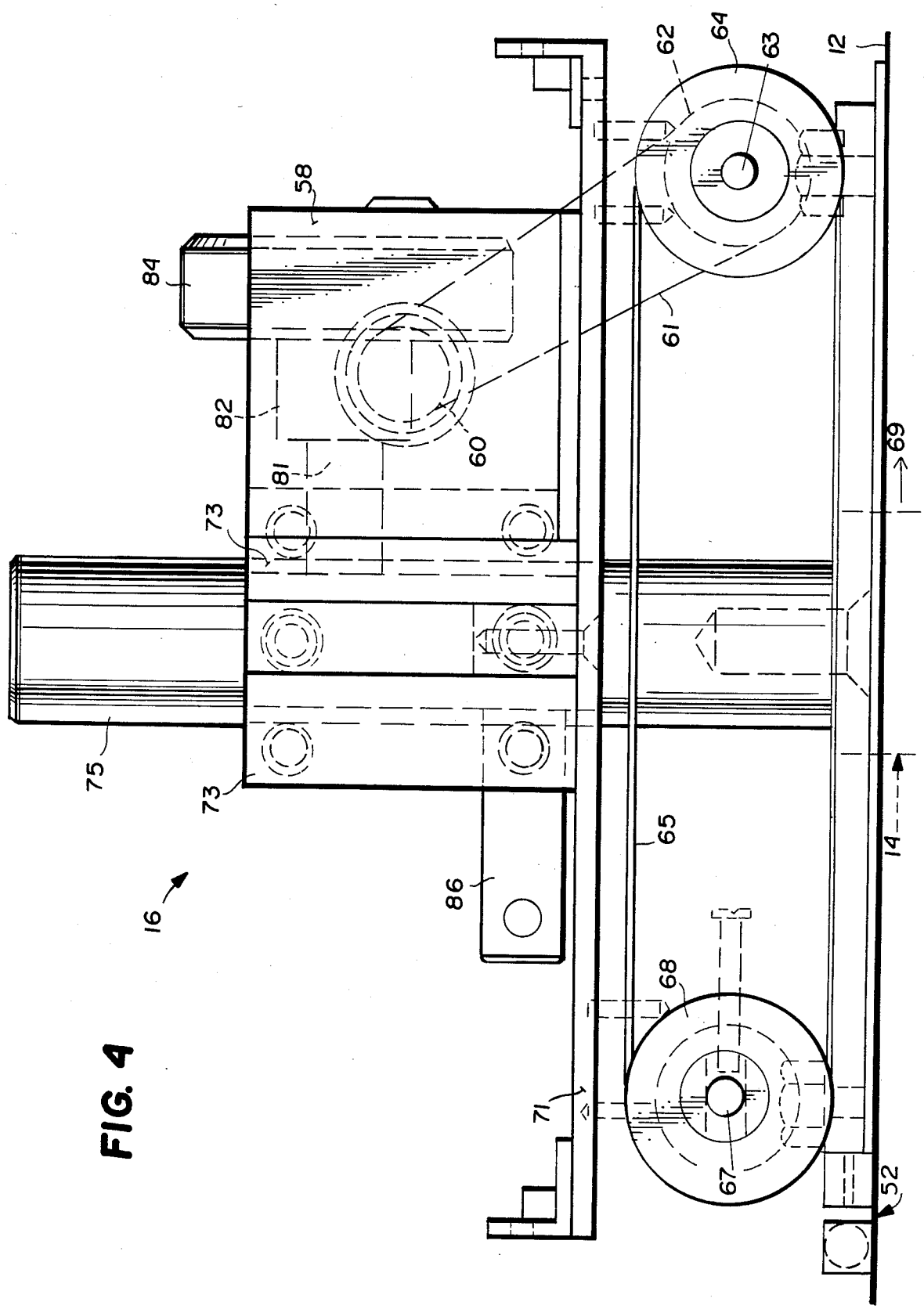
FIG. 4 is a side view of the mechanical automatic fabric swatch moving means illustrated in FIG. 1.

In order to effectively practice the continuous method according to the invention, it is desirable to use a mechanical means for continuously moving the swatch 28 of non-solid-shade fabric with respect to the colorimeter 10. An exemplary apparatus 16 for this purpose is illustrated schematically in FIG. 1, and in more detail in FIGS. 4 and 5. The apparatus 16 preferably includes swatch detection means 52 mounted at the "front" of the assembly 16 on a first side of the viewing port 14. Preferably a pair of detection means 52 are provided, one on either side of the port 14, and are for detecting a non-rigid fabric swatch 28 (i.e. an unbacked swatch 28). The detection means 52 preferably comprise optical detectors, such as those having a light source 53 and a photocell 54 (illustrated schematically in FIG. 5), which may be connected up through a conventional time delay 56 to an electric motor 58 which comprises power means for the apparatus 16.

The apparatus also includes swatch moving means, including the motor 58. The swatch moving means include the shaft 59 of the motor 58 which has a drive element, such as sprocket 60, connected thereto, and which is connected by chain 61 or the like to a driven element, such as sprocket 62, attached to a shaft 63 of a first swatch transport roller 64. The roller 64 is mounted for rotation about an axis A—A (see FIG. 5) which is generally parallel to the surface 12. The roller 64 is connected by a belt 65 to a second roller 68 mounted on the opposite side of the port 14 from the roller 64. The roller 68 is rotatable about shaft 67, which defines an axis of rotation which is generally parallel to the axis A—A. A fabric swatch 28 passes into operative association with the detection means 52, and between the belt 65 and the surface 22 to be conveyed by the belt 65 past the port 14.

The operation of the transport apparatus is such that when a fabric swatch 28 (see the schematic illustration of a portion of a swatch 28 in FIG. 5) is moved into operative association with the detectors 52, the motor 58 is started, causing the roller 64 to be driven by sprockets 60, 62 and chain 61. This causes, in turn, the belt 65 to be driven, which transports the swatch 28 in the direction of arrow 69 in FIG. 4 so that the swatch moves past the viewing port 14 and continuous measurements can be taken. The belt 65 provides the "background" for the port 14. Conveyance of the swatch in the direction 69 continues until the swatch is no longer detected by detecting means 52, at which time, after a delay of, for example, wwo seconds occasioned by the conventional time delay 56, the motor 58 is turned off, the swatch having cleared the port 14. The apparatus 16 thus allows the swatch to be continuously conveyed across the viewing port 14 at a constant speed in any uniform manner so that the readings taken by the colorimeter 10 will be uniform across the entire length of the swatch 28.

It is also desirable to provide associated with the mechanism 16 an adjustment means for adjusting the position of the belt 65 with respect to the surface 12 to accommodate the swatches of different thickness dimension (e.g. to accommodate pile fabrics as well as conventional woven fabrics) The adjustment means preferably includes, as illustrated in the drawings, a mounting base 71 which mounts the motor 58, the journals for the shaft 63, 67, and the like. The mounting base 71 is connected by arms 73 to an upright shaft or post 75, which extends generally perpendicular to the surface 12. On the backside of the post 75 a conventional rack 77 is provided (see FIG. 5) which cooperates with a conventional pinion 79. The pinion 79 is mounted for rotation with a shaft 81, which is journaled in bushing 82. The bushing 82 is mounted so that it is stationary with respect to the base 71 by any suitable arrangement (not shown).

Rotation of the shaft 81 is effected by turning the thumb wheel 84. Rotation of thumb wheel 84 effects rotation of pinion 79 and thereby vertical translation of the arm 73 with respect to the post 75 due to interengagement between the pinion 79 and rack 77.

In order to maintain the transport apparatus at a position to which it has been adjusted with respect to the post 75, any suitable clamping arrangement may be provided. For example by a movement of lever 86 the arms 73 can be moved toward and away from each other, when moved toward each other tightly clamping the post 75 therebetween so that the position of the mounting base 71 with respect to the post 75 is stabilized, and when moved away from each other allowing vertical adjustment of the position of the base 71 with respect to the post 75 by rotation of the thumb wheel 84.

The unit 16 is compact and essentially complete, and may be retrofit onto conventional colorimeters 10 merely by mounting at the post 75 to the surface 12 utilizing a mounting plate 88, or the like, which can be connected by screw threaded fasteners, or in any other desired manner, to the surface 12.

In order to facilitate movement of the sample swatch across the port 14 in any direction, while maintaining an optically acceptable viewing surface, it is desirable to provide the colorimeter 10 with positive pressure, as shown in U.S. Pat. No. 4,346,997.

It will thus be seen that according to the present invention a method and apparatus are provided for accurately and quickly determining the average color, and excursions outside the acceptable limits, of fabric swatches. The invention is applicable not only to solid-shade color swatches, but also to non-solid-shade swatches such as denim, crushed velour fabrics, patterned fabrics, and the like. While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and methods.

What is claimed is:

1. A method of determining the average color and/or excursions outside predetermined acceptable color limits of non-solid-shade fabrics, utilizing a colorimeter head, A/D converter, and computer means, comprising the steps of:
   (a) continuously moving a swatch of non-solid-shade fabric with respect to the colorimeter head;
   (b) continuously sampling the swatch with the colorimeter head, at a rate of at least about 100 readings/second, until the length of the entire swatch has been sampled and analog signals have been generated for all readings;
   (c) continuously passing the analog signals from the colorimeter head directly to the A/D convertor;
   (d) continuously converting the analog signals from the colorimeter head to digital signals utilizing the A/D convertor, and passing the digital signals to storage in the computer means; and
   (e) after completion of step (b), analyzing the stored digital signals with the entire lenght of the computer means to determine average color and/or ecursions outside acceptable limits of color, for the non-solid-shade fabric swatch.

2. A method as recited in claim 1 wherein the swatch is a non-rigid swatch, and wherein step (a) is practiced mechanically.

3. A method as recited in claim 1 wherein the non-solid-shade fabric is selected from the group consisting essentially of denim, patterned fabrics, crushed velours, pile fabrics, and fabrics containing fancy yarns.

4. A method a recited in claim 1 wherein the section of swatch sampled has a length significantly greater than 12 inches and step (b) is pacticed so that approximately 400-1,000 sample readings are taken.

5. Apparatus for determining the color of swatches of fabric, having a length significantly greater than its width comprising:
   (a) a filter colorimeter head for continuously sampling a swatch along its entire length;
   (b) an A/D converter directly connected to the filter colorimeter head for receiving analog signals from the colorimeter head and converting them to digital signals;
   (c) computer means directly connected to the A/D convertor to receive digital signals from the A/D convertor and store them, and subsequently for analyzing the stored digital signals to determine average color of the swatch, and
   (d) means for moving the swatch of fabric continuously past, and in operative association with, said colorimeter head.

6. Apparatus as recited in claim 5 wherein said colorimeter head has a housing with a generally planar surface having a viewing port therein in operative association with the colorimeter head; and wherein said swatch moving means comprises:
   swatch detection means mounted on said generally planar surface at a first side of said port;
   swatch moving means mounted on said generally planar surface and extending from said swatch detection means toward and to a second side of said port, opposite said first side, for engaging the swatch of fabric when resting on said housing generally planar surface and moving the fabric from said first side of said port to said second side thereof; said means including power means; and
   adjustment means for adjusting the position of said swatch moving means with respect to said housing generally planar surface to accommodate fabric swatches of different dimensions.

7. Apparatus as recited in claim 6 further comprising means interconnecting said swatch detection means and said power means for turning on said power means when a swatch is detected by said swatch detection means, and turning off said power means after a predetermined time delay once a swatch of fabric is no longer detected by said detection means.

8. Apparatus as recited in claim 6 wherein said swatch moving means comprises a first roller rotatable about an axis generally parallel to said planar surface, and mounted for rotation with respect to said surface adjacent said swatch detection means; a second roller rotatable about an axis generally parallel to said first roller, and mounted on the opposite side of said port from said first roller; transport belt means interconnecting said first and second rollers and for engaging a swatch of fabric; and drive means interconnecting said power means and at least one of said rollers for effecting rotation of said rollers about said axes and movement of said belt with respect to said rollers.

9. Apparatus as recited in claim 5 wherein said colorimeter head includes an electrically powered light source; and further comprising means for monitoring the voltage to said light source to calibrate the digital signals from the A/D convertor depending upon the voltage to said light source.

10. Apparatus for determining the color of swatches of fabric, comprising:
    (a) a filter colorimeter head in a housing, including an electrically powered light source, and capable of taking at least 100 readings/second of a swatch of fabric continuously moved with respect to the colorimeter head;
    (b) an A/D convertor directly connected to the filter colorimeter head for receiving analog signals from the colorimeter head and converting them to digital signals;
    (c) computer means directly connected to the A/D convertor to receive digital signals from the A/D convertor and store them, and subsequently for analyzing the stored digital signals to determine an average color of the switch; and
    (d) means for monitoring the voltage to said light source to calibrate the digital signals from the A/D convertor depending on the voltage to said light source.

11. Apparatus for moving a swatch of fabric with respect to a colorimeter head, comprising:
    (a) a filter colorimeter head having a housing with a generally planar surface having a viewing port therein in operative association with the colorimeter head;
    (b) swatch detection means mounted on said generally planar surface at first side of said viewing port;
    (c) swatch moving means mounted on said generally planar surface and extending from said swatch detection means toward and to a second side of said viewing port, opposite said first side, for engaging a swatch of fabric resting on said housing generally planar surface and moving the fabric from said first side of said viewing port to said second side thereof; said means including power means; and
    (d) adjustment means for adjusting the position of said swatch moving means with respect to said housing generally planar surface to accommodate fabric swatches of different dimensions.

12. Apparatus as recited in claim 11 wherein said swatch moving means comprises a first roller rotatable about an axis generally parallel to said planar surface, and mounted for rotation with respect to said surface adjacent said swatch detection means; a second roller rotatable about an axis generally parallel to said first roller, and mounted on the opposite side of said port from said first roller; transport belt means interconnecting said first and second rollers and for engaging a swatch of fabric; and drive means interconnecting said power means and at least one of said rollers for effecting rotation of said rollers about said axes and movement of said belt with respect to said rollers.

13. Apparatus as recited in claim 12 wherein said adjustment means comprises a mounting base for mounting said power means, rollers, and drive means; an upright post; a portion of said mounting base receiving said post and guiding said mounting base for vertical movement on, and with respect to, said post; a rack provided on said post and extending vertically; a pinion engaging said rack and mounted for rotation with respect to said post so that rotation of said pinion results in reciprocation of said mounting base with respect to said post; and clamping means for clamping said mounting base to desired positions to which it has been moved with respect to said post.

14. Apparatus as recited in claim 11 further comprising means interconnecting said swatch detection means and said power means for turning on said power means when a swatch is detected by said swatch detection means, and turning off said power means after a predetermined time delay once a swatch of fabric is no longer detected by said detection means.

15. Apparatus as recited in claim 11 wherein said detection means comprises optical detecting means.

16. Apparatus as recited in claim 11 wherein said detection means comprises first and second detection means mounted on opposite sides of said swatch moving means and for detecting a non-rigid fabric swatch.

17. Apparatus as recited in claim 11 wherein said swatch moving means comprises means for moving a non-rigid fabric swatch.

18. A method of determining color of non-rigid fabric swatches, utilizing a colorimeter head including an electrically powered light source, an A/D convertor, and computer means, comprising the steps of:
(a) continuously moving a swatch of non-rigid fabric with respect to the colorimeter head light source;
(b) continuously sampling the swatch with the colorimeter head until the length of the entire swatch has been sampled and analog signals have been generated for all readings;
(c) continuously converting the analog signals from the colorimeter head to digital signals utilizing the A/D convertor, and passing the digital signals to storage in the computer means;
(d) monitoring the voltage to the light source to calibrate the digital signals from the A/D convertor to the computer means depending upon the voltage; and
(e) after completion of step (b), analyzing the stored digital signals with the computer means to determine average coloration of the fabric swatch.

19. A method as recited in claim 18 wherein the colorimeter head has a head with an open viewing port, and comprising the steps of continuously supplying fluid under pressure to the head to exhaust through the viewing port to prevent swatch lint and dust from entering the head, to facilitate removal of heat generated by the colorimeter head, and to facilitate maintenance of the swatch so that a flat, distortion-free surface can be examined; and exhausting the fluid supplied to the colorimeter head head from a location distinct from the viewing port when the viewing port is covered by a swatch to be examined.

20. A method as recited in claim 18, wherein the section of swatch sampled has a length significantly greater than 12 inches and step (b) is practiced so that approximately 400–1,000 sample readings are taken.

* * * * *

UNITED STATES PATENT AND TRADEMARK OFFICE
CERTIFICATE OF CORRECTION

PATENT NO. : 4,788,650

DATED : November 29, 1988

INVENTOR(S) : Willis et al

It is certified that error appears in the above-identified patent and that said Letters Patent is hereby corrected as shown below:

Column 2, lines 32-33, "operativey" should read --operatively--; line 43, ".idse" should read --side--. Column 5, line 66, "wwo" should read --two--. Column 7, line 20, delete "entire lenght of the"; line 22, "ecursions" should read --excursions--; and after "the" insert --entire length of the--.

Signed and Sealed this

Tenth Day of April, 1990

*Attest:*

HARRY F. MANBECK, JR.

*Attesting Officer*  *Commissioner of Patents and Trademarks*